US006965798B2

(12) United States Patent
Kim (10) Patent No.: US 6,965,798 B2
(45) Date of Patent: Nov. 15, 2005

(54) IMPLANTABLE DEVICE FOR TREATING ATRIAL FIBRILLATION AND METHOD OF USING SAME

(76) Inventor: Young D. Kim, 1008 Gelston Cir., McLean, VA (US) 22102

( * ) Notice: Subject to any disclaimer, the term of this patent is extended or adjusted under 35 U.S.C. 154(b) by 529 days.

(21) Appl. No.: 10/318,298

(22) Filed: Dec. 13, 2002

(65) Prior Publication Data

US 2003/0233128 A1 Dec. 18, 2003

Related U.S. Application Data

(60) Provisional application No. 60/388,772, filed on Jun. 17, 2002.

(51) Int. Cl.[7] .............................................. A61N 1/00
(52) U.S. Cl. ......................... 607/120; 607/129; 607/3
(58) Field of Search ............................. 607/3, 119–156

(56) References Cited

U.S. PATENT DOCUMENTS

| 5,269,326 A | 12/1993 | Verrier |
| 5,741,322 A | 4/1998 | Mehmanesh et al. |
| 5,849,033 A | 12/1998 | Mehmanesh et al. |
| 5,928,278 A | 7/1999 | Kitschmann |
| 5,968,010 A | 10/1999 | Waxman et al. |
| 6,152,955 A | 11/2000 | Knight et al. |
| 6,324,435 B1 | 11/2001 | Shchervinsky et al. |
| 6,330,481 B1 | 12/2001 | Van Wijk et al. |
| 6,385,491 B1 | 5/2002 | Lindemans et al. |
| 6,463,335 B1 | 10/2002 | Münch et al. |
| 2002/0035388 A1 | 3/2002 | Lindemans et al. |

FOREIGN PATENT DOCUMENTS

FR  2 799 128  4/2000

OTHER PUBLICATIONS http://www.guidant.com/products/aicd.shtml; Dec. 2, 2002; AICD—Automatic Implantable Cardioverter Defibrillators; pp. 1-40; © 2002, Guidant Corporation.

Primary Examiner—Scott M. Getzow
(74) Attorney, Agent, or Firm—Foley & Lardner

(57) ABSTRACT

A device for treating atrial fibrillation includes a pad which houses the distal end of an electrode which is adapted to deliver a substantially uniform shock gradient to an atrial surface of a postoperative cardiac patient, if atrial fibrillation is detected. The device also includes a catheter for delivering anti-arrhythmic and/or anesthetic drugs to the pad. After a treatment period, the device may be removed by pulling the electrode and the pad, if the pad is not bioabsorbable, into the catheter and then pulling the catheter through the patient's chest wall.

47 Claims, 5 Drawing Sheets

IMPLANTABLE DEVICE FOR TREATING ATRIAL FIBRILLATION AND METHOD OF USING SAME

CROSS-REFERENCE TO RELATED APPLICATIONS

This application claims priority to U.S. Provisional Patent Application Ser. No. 60/388,772, filed on Jun. 17, 2002, the contents of which are hereby incorporated by reference.

BACKGROUND OF THE INVENTION

1. Field of the Invention

The present invention relates to preventing and treating atrial fibrillation. More particularly this invention relates an apparatus and method temporarily used to prevent and/or treat atrial rhythm disturbances in postoperative cardiac patients.

2. Description of the Related Art

Atrial fibrillation is the most common postoperative cardiac rhythm disturbance, occurring in about 30–40% of all adult cardiac surgery patients. In addition, atrial fibrillation often induces hemodynamic instability and/or increases thromboembolic events. As a result, the high incident rate of atrial fibrillation is the leading cause of prolonged hospitalization after cardiac surgery. Further, the cost associated with this prolonged stay is high both from a viewpoint of the amount of money the stay costs the patient (or his insurance carrier) and from the viewpoint of the patient's lost ability to earn money through work.

Paradoxically, despite the numerous preventive improvements and measures that have arisen in surgical/cadiopulmonary bypass techniques, the incident rate of atrial fibrillation has increased in recent years. Although many preoperative and postoperative factors have been implicated, the precise mechanism responsible for the high incidence of atrial fibrillation in postoperative patients remains unknown.

In response to postoperative atrial fibrillation, current practice dictates pharmacological treatments and/or electrical shock conversion. Treatment of atrial fibrillation pharmacologically often fails and requires electrical shock conversion. In addition, maintaining the sinus rhythm after successful carioversion has proven to be quite difficult and, therefore, the recurrent rate is extremely high without systemic administration (orally or intravenously) of anti-arrhythmic drugs. For this reason, it is mandatory to administer anti-arrhythmic drugs for at least the recovery period. However, such systemic administration of drugs can be associated with significant side effects.

Intravenous procainamide is often used since it can reach therapeutic levels rather rapidly. However, procainamide can cause ventricular depression, hypotension, prolongation in the QT portion of the electrocardiogram, and/or ventricular fibrillation. As a result, careful monitoring of the procainamide serum levels is required. Further, maintaining optimum serum levels is difficult. Similarly, rapid intravenous infusion of amiodarone may cause significant ventricular depression/bradycardia. As a result, it is recommended to build the therapeutic level of amiodarone slowly, i.e., by taking between about 24 and about 48 hours. In addition, other long-term side effects of amiodarone may include injury to the lungs, thyroid, skin, and/or nervous system.

The undesirable systemic side effects from these drugs stem from the relatively high circulating levels of the drugs which needed are to raise their concentration in the atrial tissue. Therefore, it is desirable to deliver drugs to the atrial tissues without administering the drugs systemically. If the drugs were delivered directly to the atrial tissue, only a fraction of the systemic dose of the drugs would be needed to adequately raise their concentration in the atrial tissue, thereby achieving anti-atrial fibrillation effects without inducing systemic side effects. Procainamide is well known to infiltrate tissue readily and amiodarone is a lipophylic substance and is expected to infiltrate atrial tissue as well as procainamide. Ayers et al. demonstrated the effectiveness in suppressing atrial fibrillation using amiodarone instilled into a canine's pericardial sac. J. Cardiovascular Electrophysiology, vol. 7, no. 8, (August, 1996).

It is possible, of course, to deliver drugs directly to the pericardial sac after transvenously passing a catheter to the right atrium and thereafter transatrially puncturing the atrial wall, thereby providing access to the pericardial sac. See, e.g., U.S. Pat. Nos. 5,269,326 and 5,968,010. However, these approaches are very invasive and technically difficult and, therefore, carry significant risks. For this reason, systemic pharmacological treatments, with and without external electric shock, remains the preferred method of addressing atrial fibrillation in patients recovering from cardiac surgery.

Hemodynamic instability from atrial fibrillation or failure of pharmacological treatment of atrial fibrillation mandates electric shock defibrillation. Conventional external electric defibrillation procedures require high electrical energy (i.e., on the order of 100–300 joules) and, as a result of the intense shock and patient discomfort associated therewith, are preferably delivered after general anesthesia or deep sedation, both of which are time consuming procedures. In addition, as a result of the necessary anesthesia or sedation, external shock may require the presence of an anesthesiologist, a cardiologist, and an intensivist. Finally, the procedure itself is not without substantial risk; the human cost associated with external shock can include disturbing cardiac stability to the point where the patient may die.

Rapidly converting atrial fibrillation back to sinus is known to reduce the predisposition for intractable/additional episodes of atrial fibrillation. Implantable atrial cardioconverters ("IACs"), at least in theory, are an excellent device for detecting and rapidly converting atrial fibrillation. Further, IACs have been introduced to manage chronic atrial fibrillation and have proven to be safe and effective.

The standard lead configuration for IACs delivers a shock between electrodes in the right atrial appendage and the coronary sinus. As a result of this configuration, the posterior of the left atrium is exposed to the lowest shock and, therefore, often yields the lowest potential gradient in this region. Further, the lowest gradient often yields the earliest activation leading to an unsuccessful shock. To prevent this problem, IACs deliver about 3 to about 6 joules of energy, which may cause noticeable discomfort.

Unfortunately, associated with IACs are the following drawbacks: (a) discomfort from the shock provided by the device which is exacerbated by the frequent rate at which the shocks are administered; (b) a poor cost/effectiveness ratio; and (c) technical problems associated with the device which can not be readily addressed due to its being permanently implanted. As a result, IACs are no longer being used for chronic atrial fibrillation, unless coupled with an automated ventricular converter. Recently, an implantable atrial defibrillation (the Syncrus system of the Guidant Corporation) has been introduced for postoperative atrial fibrillation. However, this implantable atrial converter, which uses biatrial wires, requires a higher range of energy (e.g., 3–10 joules) for a successful cardioversion and, therefore, causes similar discomfort as in the aforementioned IAC.

There have been several previous improvements to treat postoperative atrial fibrillation. A first example involves covering more surface area of the atrium with the electrode (i.e., the electrode either winds around the surface of the atrium or divides into multiple wires each of which is directed toward a different portion of the surface area of the atrium). See, e.g., U.S. Pat. Nos. 5,741,322, 5,849,033, 5,928,278, 6,152,955, 6,324,435, 6,330,481, 6,385,491, 6,463,335, and U.S. patent application Publication 2002/0035388. By covering more of the atrial surface area, a more uniform shock may be applied to the atrium thereby increasing the likelihood of a successful shock.

In an attempt to address the lack of uniformity in the potential gradient, the electrodes in the aforementioned patents and patent application have been incorporated into pads which cover a greater portion of the atrial surface area. In addition, these pads may be bioabsorbable. See, e.g., U.S. Pat. Nos. 5,849,033, 6,330,481, 6,324,435, 6,385,491, 6,463,335, and U.S. patent application Publication 2002/0035388. By housing the electrode in a bioabsorbable pad, the electrode can easily be removed by pulling it through the patient's chest wall after the pad is absorbed thereby eliminating the need to open the chest cavity a second time. Unfortunately, however, the pads are bulky, present adhesion problems (due to the rounded shape of the heart and due to the fact that the heart's size continuously expands and contracts), and may interfere with the beating of the heart by inhibiting the ability of the atrium to expand.

Electrode pads have also been used to deliver time-release quantities of antiarrhythmic drugs. See, e.g., U.S. Pat. No. 6,385,491 and U.S. patent application Publication 2002/0035388. Unfortunately, the amount of drug delivered according to these methods is not controllable, i.e., the drug type, timing, and dosage is predetermined; the drug type and/or dosage can not be increased or decreased in response to changes in a patient's condition.

Accordingly, what is needed is a new method and apparatus which: (a) can successfully defibrillate an atrium while delivering a quantum of energy that a conscious and non-sedated patient will either not notice or easily tolerate; (b) is able to deliver antiarrhythmic medication directly to the atriums which will eliminate (or at least minimize) the aforementioned side effects caused by systemic exposure to high concentrations of antiarrhythmic drugs; and/or (c) has the ability to control drug delivery directly to the atriums in terms of drug type, timing, and/or dosage.

SUMMARY OF THE INVENTION

The invention herein contains multiple embodiments including a first device for treating atrial fibrillation in a postoperative cardiac patient. This first device includes a bioabsorbable pad adapted to be placed on an atrial surface of the patient, an electrode a distal end of which is provided in the pad, and a catheter adapted to deliver at least one drug to the pad. In this device, the distal end of the electrode is adapted to deliver a substantially uniform electrical shock to the atrial surface. In addition, a proximal end of the electrode is adapted to be connected to an energy source.

In a further embodiment of the first device, the distal end of electrode may include a plurality of electrode portions.

In another further embodiment of the first device, the distal and proximal ends of the electrode may be electrically connected by a central wire. Further, the wire may be provided in a lumen in the catheter.

In another further embodiment of the first device, the at least one drug may comprise at least one anti-arrhythmic drug such as, for example, procainamide, amiodarone, a combination of procainamide and at least one other anti-arrhythmic drug, a combination of amiodarone and at least one other anti-arrhythmic drug, or a combination of procainamide, amiodarone and at least one other anti-arrhythmic drug. Further, the at least one drug may also comprise at least one anesthetic drug such as, for example, procaine, lidocaine, a combination of procaine and at least one other anesthetic drug, a combination of lidocaine and at least one other anesthetic drug, or a combination of procaine, lidocaine, and at least one other anesthetic drug.

In another further embodiment of the first device, the substantially uniform electrical shock delivered to the atrial surface may be in the form of a predetermined amount of energy of about 1.0 joules and about 3.0 joules.

In another further embodiment of the first device, the distal end of electrode may include a plurality of electrode portions. Further, the plurality of electrode portions may comprise between 4 and 8 electrode portions arranged in a petal-like arrangement fanning out from a central hub. In addition, each of the petal-like electrodes may be exposed on one side thereof whereas an opposite side of the petal-like electrodes may be in contact with an underside the pad. Moreover, an insulating material may be provided on a topside of the pad whereas an adhesive material (such as, for example, gelatin, silicon, protein polymers, collagen pellets, and thrombin) may be provided on the underside of the pad.

In another further embodiment of the first device, the distal end of electrode may include a plurality of electrode portions. Further, the plurality of electrode portions may comprise between 4 and 8 electrode portions arranged in a petal-like arrangement fanning out from a central hub each of which is associated with a corresponding petal-like portion of the pad. In addition, the pad may be formed of a polymeric material.

In another further embodiment of the first device, the pad may be formed of a polymeric material which may be sponge or which may be knitted or woven.

In another further embodiment of the first device, the distal end of electrode and the pad may be spiral shaped.

In another further embodiment of the first device, the device may also include a pacing wire adapted to provide pacing energy to the atrial surface of the patient.

The invention also involves a second device for treating atrial fibrillation in a postoperative cardiac patient. This device includes: (a) a first bioabsorbable pad adapted to be placed on an atrial surface of a right atrium of the patient; (b) a first electrode a distal end of which is provided in the first pad, wherein the distal end of the first electrode is adapted to deliver a substantially uniform electrical shock to the atrial surface of the right atrium, and wherein a proximal end of the first electrode is adapted to be electrically connected to an energy source; (c) a second bioabsorbable pad adapted to be placed on an atrial surface of a left atrium of the patient; (d) a second electrode a distal end of which is provided in the second pad, wherein the distal end of the second electrode is adapted to deliver a substantially uniform electrical shock to the atrial surface of the left atrium, and wherein a proximal end of the second electrode is adapted to be connected electrically to the energy source; and (e) at least one catheter adapted to deliver at least one drug to at least one of said right and left atrial surfaces.

In a further embodiment of the second device, each of the distal ends of the first and second electrodes may comprise a plurality of electrode portions provided in a fan-like arrangement.

In another further embodiment of the second device, each of the electrodes may have a central portion between the distal and proximal ends thereof. In addition, the central portion of at least one of said electrodes may be provided in a lumen in the catheter.

In another further embodiment of the second device, the at least one drug may comprise an anti-arrhythmic drug. In addition, the at least one drug may also comprise an anesthetic drug.

In another further embodiment of the second device, the substantially uniform electrical shocks delivered to the atrial surfaces of the right atrium and the left atrium may comprise a predetermined amounts of energy. In addition, each of the predetermined amounts of energy may be between about 1.0 joules and about 3.0 joules.

In another further embodiment of the second device, the at least one catheter may comprise two catheters. In addition, a first of said catheters may be adapted to deliver the at least one drug to the right atrial surface whereas a second of said catheters may be adapted to deliver the at least one drug to the left atrial surface. Further, each of the electrodes may have a central portion between the distal and proximal ends thereof, wherein the central portion of the first electrode is provided in a lumen in the first catheter, and wherein the central portion of the second electrode is provided in a lumen in the second catheter.

In another further embodiment of the second device, the device may also include at least one pacing wire adapted to provide pacing energy to at least one of the right and left atrial surfaces of the patient.

The invention also contemplates a method of treating atrial fibrillation in a postoperative cardiac patient. This method includes: (a) placing a bioabsorbable pad on an atrial surface of the patient, wherein the pad contains a distal end of an electrode which is adapted to deliver a substantially uniform electrical shock to the atrial surface; (b) passing a proximal end of the electrode through a chest wall of the patient; (c) connecting the proximal end of the electrode to an energy source; (d) monitoring the atrial surface for atrial fibrillation; if atrial fibrillation is detected, (e) shocking the atrial surface with a predetermined amount of energy to defibrillate the heart; and (f) delivering at least one drug to the pad in contact with the atrial surface via a catheter passing through the chest wall. In this method the energy is delivered from the energy source to the atrial surface via the electrode.

In a further embodiment of the method, the predetermined amount of energy may be between about 1.0 joules and about 3.0 joules.

In another further embodiment of the method, the distal end of electrode may comprise a plurality of electrode portions provided in a fan-like arrangement.

In another further embodiment of the method, the distal and proximal ends of the electrode may be electrically connected by a central wire. Further, the wire may be provided in a lumen in the catheter.

In another further embodiment of the method, the at least one drug may comprise an anti-arrhythmic drug. Further, the at least one drug may also comprise an anesthetic drug.

In another further embodiment of the method, the at least one drug may comprise an anesthetic drug. In addition, the method may further include: (d)(1) anesthetizing locally tissue surrounding the heart with the anesthetic drug before the step of (e) shocking the atrial surface with a predetermined amount of energy to defibrillate the heart. Further, the step of (f) delivering at least one drug to the pad in contact with the atrial surface via a catheter passing through the chest wall may include: (f)(1) medicating the atrial surface with an antiarrhythmic drug either during or after the step of (e) shocking the atrial surface with a predetermined amount of energy to defibrillate the heart.

In another further embodiment of the method, the method may include: (g) bioabsorbing the pad over a treatment duration; and (h) removing the electrode from the atrial surface. In addition, the distal and proximal ends of the electrode may be electrically connected by a central wire. Further, the wire may be provided in a lumen in the catheter. Moreover, the step of (h) removing the electrode from the atrial surface may include: (h)(1) pulling the electrode through the catheter.

In another further embodiment of the method, the distal and proximal ends of the electrode may be electrically connected by a central wire provide in a lumen in the catheter. Further, the method may also include: (h) removing the electrode and the pad from the atrial surface by pulling the electrode and the pad through the catheter.

In another further embodiment of the method, the proximal ends of the electrode portions may be electrically provided in a bundle in a lumen in the catheter. Further, the method may also include: (h) removing the electrode and the pad from the atrial surface by pulling the electrode and the pad through the catheter.

In another further embodiment of the method, the step of (a) placing a bioabsorbable pad on an atrial surface of the patient, may include: (a)(1) adjusting the size of the electrode provided in the pad to correspond to the size of the atrial surface to which the pad is subsequently placed.

In another further embodiment of the method, the step of (f) delivering at least one drug to the pad in contact with the atrial surface via a catheter passing through the chest wall may include: (f)(1) delivering a bolus of the drug to the atrial surface.

In another further embodiment of the method, the step of (f) delivering at least one drug to the pad in contact with the atrial surface via a catheter passing through the chest wall may include: (f)(1) delivering the drug continuously to the atrial surface by means of a pump.

In another further embodiment of the method, the method may also include: (g) providing pacing energy to the atrial surface of the patient by means of a wire. In addition, the wire and the electrode may be provided in a catheter extending from the atrial surface of the patient to a location external of the patient's chest wall.

These and other features, aspects, and advantages of the present invention will become more apparent from the following description, appended claims, and accompanying exemplary embodiments shown in the drawings.

BRIEF DESCRIPTION OF THE DRAWINGS

The accompanying drawings, which are incorporated in and constitute a part of the specification, illustrate various embodiments of the invention and together with the description, serve to explain the principles of the invention.

DETAILED DESCRIPTION

Unlike conventional external electrical shock which requires 100–300 joules of energy much of which is absorbed by the torso of the patient, in this invention as the pads are in direct contact with the atrial walls, a small amount of energy such as between about 1.0 and 3.0 joules (and preferably less than about 2.0 joules) will be needed to defibrillate the right and left atriums. An electrical shock on this order of energy will cause the patient nearly no discomfort and, therefore, can be administered without anesthesia or sedation.

The cost of the invention for use in postoperative patients is minimal compared to implantable atrial cardioconverters used for chronic atrial fibrillation. In addition, the device is easy to place after cardiac surgery but before the patient's chest is closed; further such placement occurs without a complex delivery system.

On embodiment of the invention described herein eliminates the problems associated with single wire electrodes (regardless of whether the wire is strait or curved) by using a wire that fans into a petal-like configuration which covers a substantial portion of the atrial surface. As a result of the area covered by the petal-like electrode, the shock applied to the atrium is substantially uniform over the surface area thereof. Further, as the petal-like electrodes are preferably in direct contact with, and substantially cover the atrial surface the atrium, the amount of energy needed to defibrillate the heart may be well below that which would cause discomfort. In this configuration, the device: (a) increases the success rate of the shock; (b) reduces the amount of energy applied to the heart; and (c) improves upon the patient's overall comfort.

Figure 1:
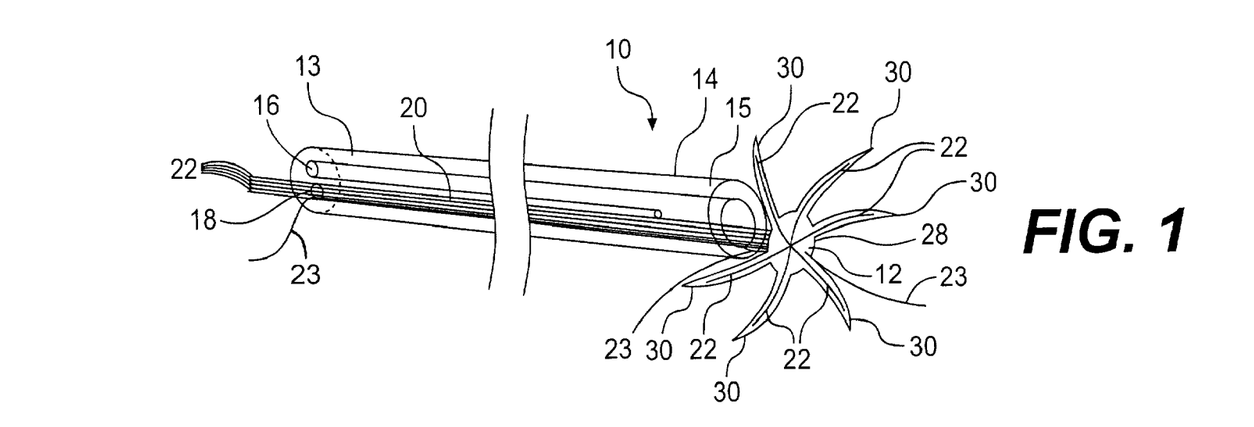
FIG. 1 is a perspective view of a device comprising an adhesion pad, and a catheter having two lumens therein.

The invention will now be discussed in detail with respect to the drawings. FIG. 1 is a perspective view of a device 10 comprising an adhesion pad 12, a catheter 14 having two lumens 16, 18 therein, and an electrode 20. The first lumen 16 may be used to transport at least one drug to the pad 12, as later described in detail. In addition, the first and second lumens 16, 18 may merge (as shown in FIG. 1) into a wide opening at a distal end 15 of the catheter 14 to aid in pulling the pad 12 into the catheter 14, as later described in detail.

The electrode 20, which is preferably housed within the second lumen 18 (as shown), comprises a plurality of bundled electrode portions 22 which are in the form of wires formed of a conductive material such as copper. A pacing wire 23, may be journalled in lumen 18 along with the electrode portions 22 (as shown); the details of the pacing wire 23 will later be discussed in detail.

If the pacing wire 23 is provided in the same lumen 18 as the electrode portions 22, the electrode portions 22 should be electrically insulated with respect to the pacing wire 23, and preferably with respect to each other. Outside of the device 10 at a distal end 15 of the catheter 14, however, the electrode portions 22 and the pacing wire 23 are electrically exposed. However, one side of the electrode portions 22 may be insulated by petal-like portions 30 of the pad 12, as later described in detail.

For ease of reference and understanding, the catheter 14 is shown as being transparent. However, the catheter need not be transparent. Preferably, the catheter 14 is insulated and formed of a synthetic material such as PVC or polyurethane. In addition, the catheter 14, which may be a standard central venous pressure catheter or intravenous catheter, is about 16 gauge in size and is long enough to extend from an atrial surface of a patient to a location external of the patient's chest wall 40, i.e., a length of at least about 40 cm to about 60 cm.

Preferably the electrode bundle 20 comprises between four and eight electrode portions 22. As the electrode portions 22 emerge from the distal end 15 of the catheter 14, they pass through a central hub 28 portion of the pad 12 from a topside 32 to an underside 34 of the pad 12. After passing through the pad 12, the electrode portions 22 branch out in a petal-like manner such that each portion 22 is received by a corresponding petal-like pad portion 30 of the pad 12, i.e., the number of petal-like portions 30 preferably corresponds to the number of electrode portions 22.

Figure 2:
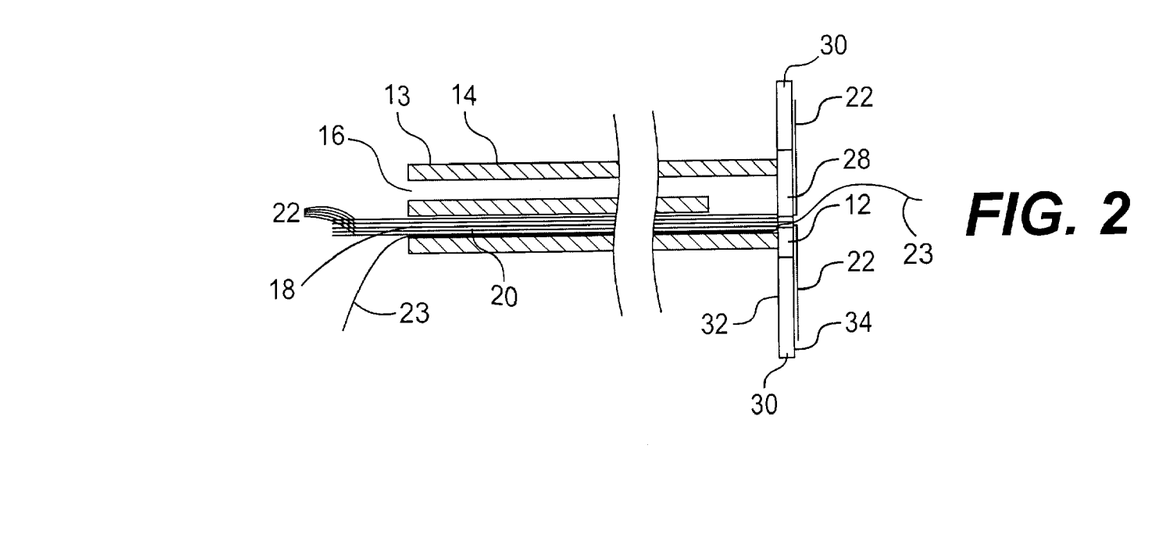
FIG. 2 is a cross-sectional side view of the device of FIG. 1.

For ease of reference and understanding in FIG. 1, the pad 12 is shown as being separated from the distal end 15 of the catheter 14 by a gap whereas, in actuality, the pad 12 may abut the distal end 15 of the catheter 14 (as shown in FIG. 2 which is a side cross-sectional view of the device 10 of FIG. 1).

The central portion 28 of the pad 12 is preferably circular in shape and has a diameter of about 5 mm whereas the petal-like portions 30 extend between about 5 cm and about 8 cm from the central portion 28. However, the length of the petal-like portions 30 (and the electrode portions 22 attached thereto) may be cut, at the time of implantation, to correspond to the size of the atrial surface to which the pad 12 will be affixed. Further, the pad 12 may be formed of a bioabsorbable material such as, for example, collagen, which will enable the pad 12 to be flexible and elastic in nature so that it can deform with the beating of an atrium to which the pad is adhered, without interfering with the beating of the atrium.

Preferably, the pad 12 is made of a conformable material in which the electrode 20 (which may be one wire or a series of wires corresponding to the electrode portions 22) divides into thin the electrode portions 22. By making the electrodes portions 22 thinner than the electrode 20, the overall thickness of the pad 12 may be reduced. Further, by making the pad thinner 12, the device 10 reduces or eliminates at least some of the aforementioned problems associated with the currently thick pads, including the previous inability of pads to deform with the beating of the heart and the related problem of inhibiting successful heart beats.

In addition, the pad 12 is preferably sponge-like and/or knitted or woven so that drugs (delivered thereto via the lumen 16) will readily diffuse via capillary through microchannels in the pad 12 to and through the petal portions 30 of the pad 12. From the petal portions 30, the drugs may be readily transmitted to a substantial portion of the surface area of the atrium to which the pad 12 adheres, for at least the recovery period. Drugs of this nature may include anti-arrhythmic drugs such as, for example, a procainamide and amiodarone. Alternatively or additionally, the drugs may include anesthetic drugs such as, for example, procaine and lidocaine.

The at least one drug may be administered continuously (by, for example, an infusion pump) or as a bolus. Further, the administering of the at least one drug may be automated with respect to a monitored level of the drug's concentration and/or in response to a perceived need such as, for example, in response to detecting atrial fibrillation.

Drugs passed through the catheter 14 may enhance defibrillation and/or provide local anesthesia to the atrium before an electrical shock, thereby reducing the discomfort suffered by a patient during the shock. As the atrial walls are thin and outlined with a loose epithelial layer, the anti-arrhythmic drugs will readily infiltrate the atrial tissue thereby enabling the drugs to prevent and/or stop atrial fibrillation. Further, by passing the anti-arrhythmic drugs through the catheter directly to the atrial walls, the atrial walls may be saturated without experiencing the previously discussed side effects.

The underside 34 of the pad 12 preferably has an adhesive applied thereto to enable the pad 12 to adhere to an atrial surface. The adhesive may be, for example, gelatin, silicon, protein polymers, collagen pellets, and/or thrombin. To insulate the tissue surrounding the heart from the energy carried in the electrode portions 22 (and correspondingly to ensure that more of the energy is directed into the atrial surface to which the pad 12 is adhered), the topside 32 of the pad 12 is preferably covered with an insulator.

Figure 3:
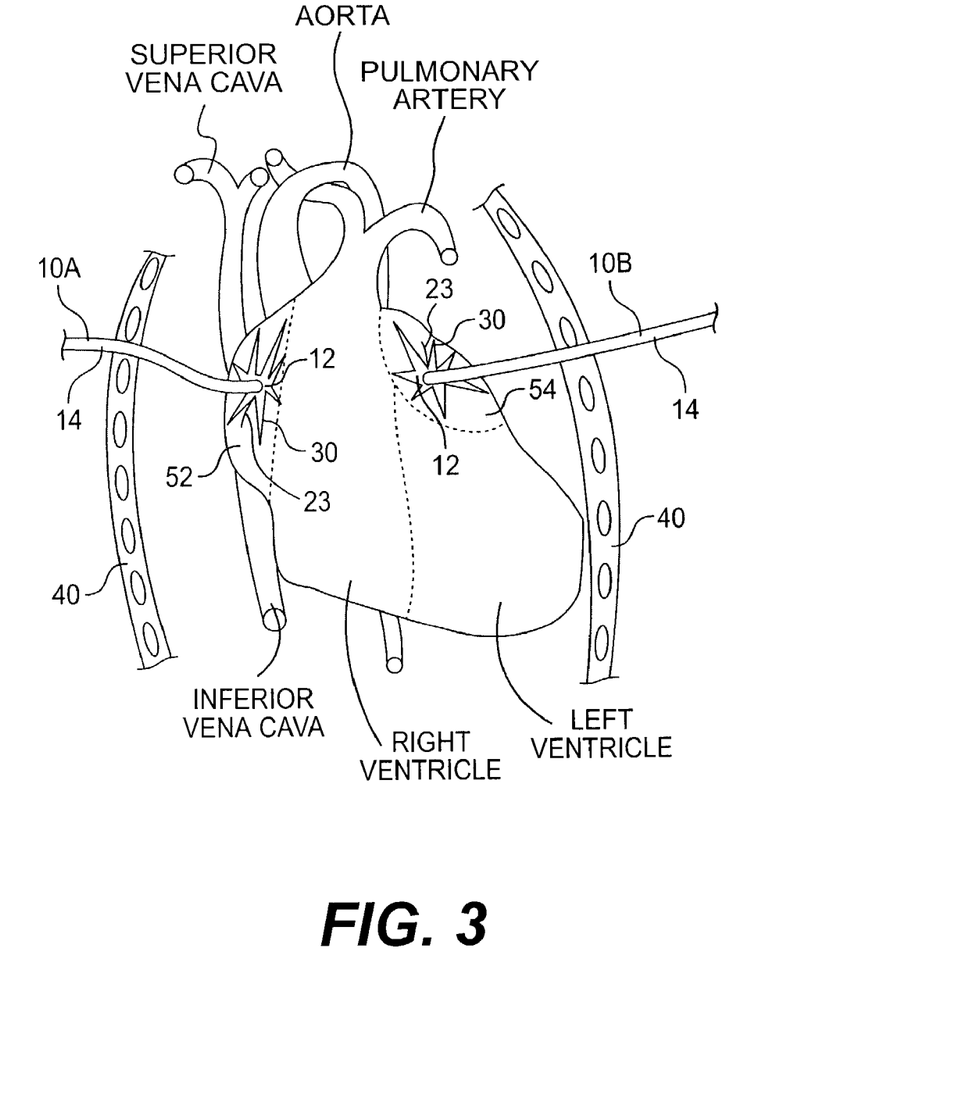
FIG. 3 is a schematic view of the heart showing two of the devices of FIG. 1, in which the pad of one of devices is adhered to the atrial surface of the right atrium and in which the pad of the other of the devices is adhered to the atrial surface of the left atrium.

FIG. 3 is a schematic view of a patient's heart showing two of the devices 10 of FIG. 1 being affixed thereto. The pad 12 of a first 10A of devices is adhered to the atrial surface of the right atrium 52 whereas the pad 12 of the second 10B of the devices is adhered to the atrial surface of the left atrium 54. The catheters 14 of the devices 10A, 10B, pass through the chest wall 40 of the patient.

In this bi-atrial embodiment of the invention, the pair of pads 12 containing the petal-like electrode portions 22 are placed on the surfaces of the atrial surfaces of the right 52 and left 54 atriums after cardiac surgery and before the patient's chest is closed. Further, by placing a device 10 on each of the atrial surfaces, the amount of energy needed may be 50% less than that needed for the situation in which one device 10 is placed on the atrial surface of one atrium 52, 54 and no device 10 is placed on the atrial surface of the other atrium 52, 54.

Regardless of the number of devices 10 used, the electrodes 20 may be used to sense the bipolar EKG wave and thereby detect atrial fibrillation. In addition, electric shocks may be administered from a biphasic wave delivery system to the atrial surface via the electrodes 20, as later discussed in detail.

Figure 4:
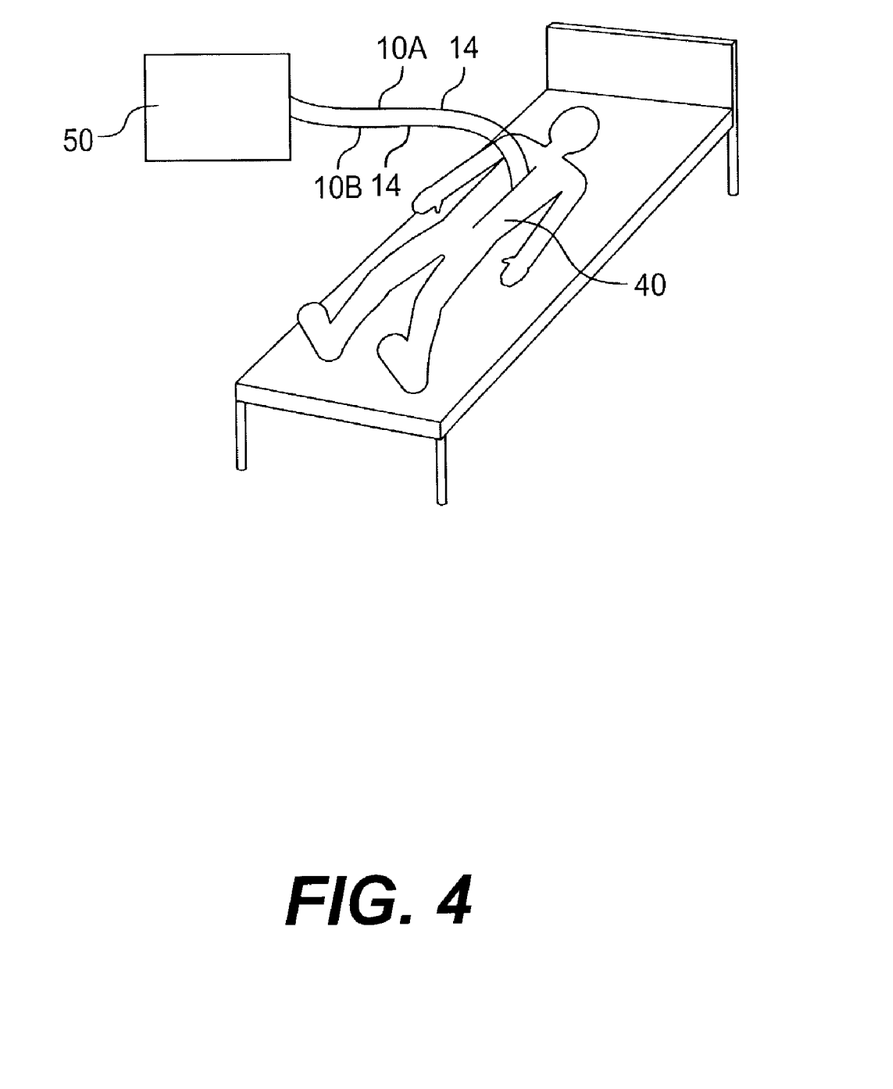
FIG. 4 is a schematic view showing the catheters of the devices of FIG. 3 protruding through the chest wall of a post operative patient and leading to monitoring and/or defibrillation equipment.

FIG. 4 is a schematic view showing catheters 14 of the devices 10A, 10B of FIG. 3 protruding through the chest wall 40 of a post operative patient, after the chest wall 40 has been closed. Although the catheters 14, in which the electrodes 20 are housed in bundle form, are shown as extending from the patient to a machine 50, the catheters 14 need only extend through the chest wall 40 at which point extension cords could connect the electrodes 20 and/or the lumens 16 to the machine 50. In addition, the machine 50 may be a EKG monitor, a defibrillator (i.e., a defibrillating power supply), a pacing device, a drug delivery device (which may be adapted to administered at least one drug either continuously or as a bolus), or a combination of any of two or more of these machines.

In one preferred embodiment, the machine 50 will monitor the patient's heart rate and will provide pacing energy through the pacing wire 23 to at least one of the atriums 52, 54 (as shown in FIG. 3). If, however, atrial fibrillation is detected (via one of the electrodes 20), the machine 50 may transmit defibrillating energy on the order of 1.0 to 3.0 joules through both of the electrodes 20 to the atrial surfaces of the right 52 and left 54 atriums.

In a further embodiment, the machine 50 may also monitor the nature of the atrial rhythm and may direct the machine 50 to administer additional quantities of an antiarrhythmic and/or anesthetic drug (e.g., procaine, procainamide, amiodarone, lidocaine, or other drug), either continuously or as a bolus, through the lumen 16 to the pad 12 from where it can diffuse into the atrial surface. Further, in addition to the amount of drug delivered, this embodiment of the device may allow the physician to control the timing at which the drug is administered, the duration over which the drug is administered, and the type of drug administered.

Figure 5:
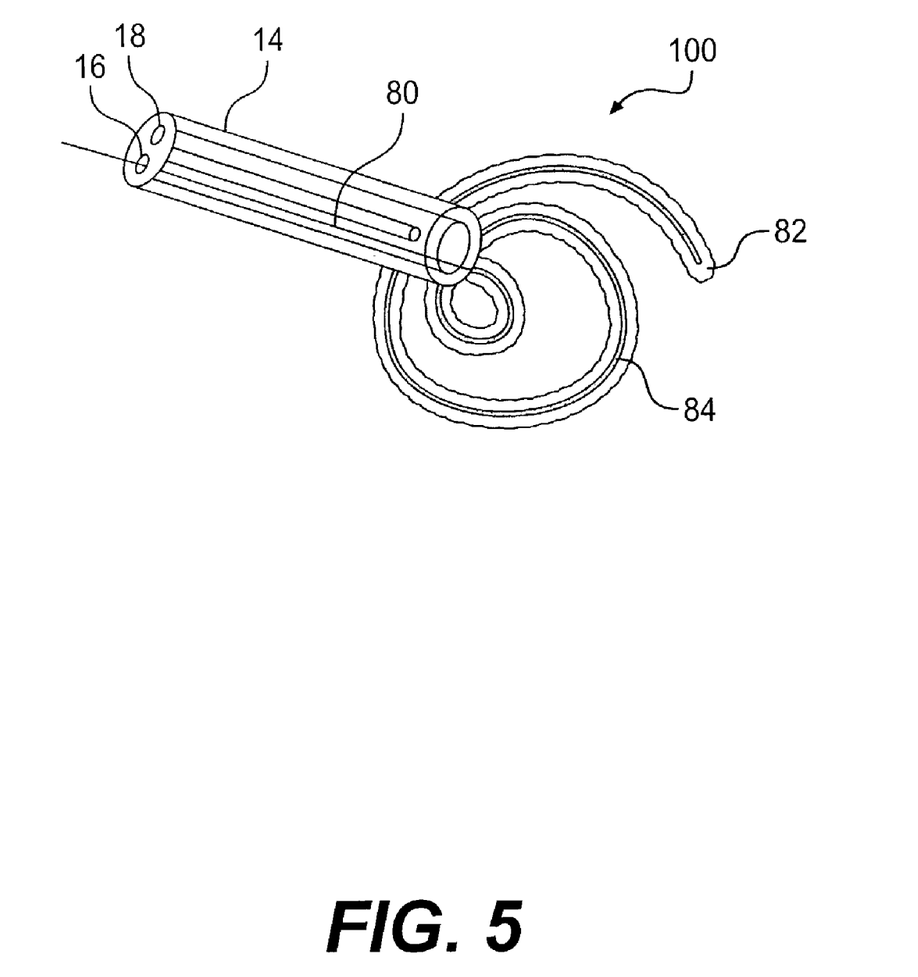
FIG. 5 is schematic view of an alternate embodiment electrode having a spiral shape.

FIG. 5 is schematic view of an alternate embodiment device 100 containing an electrode 80. In this embodiment, rather than have a bundled electrode 20 which branches into electrode portions 22 in a petal-like portions 30 of a pad 12, this embodiment uses one wire 84 incorporated into a spiral shaped pad 82. The spiral shaped pad 82 is preferably formed of the same material as the previously described pad 12, so that it will not inhibit the beating of the heart and will facilitate drug delivery to the atrial surface of an atrium 52, 54. Further, the pad 82 will similarly have an adhesive material on an underside thereof and an insulator on a topside thereof. Finally, like the previously described pad 12, the pad 82 of this embodiment may be bioabsorbable and cut prior to implantation to correspond to the size of the atrial surface area to which it will adhere.

Figure 6:
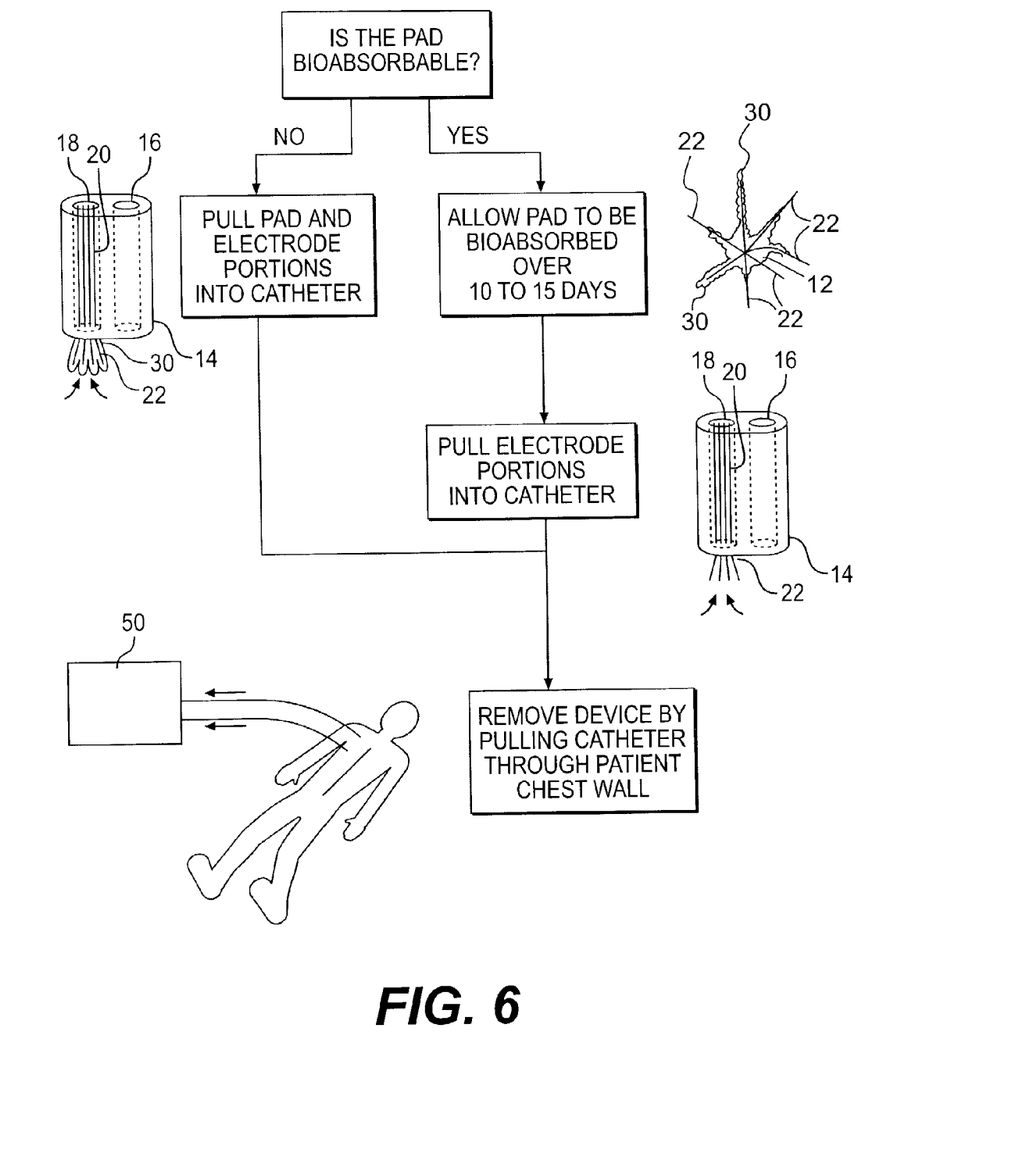
FIG. 6 is a side-by-side flow diagram showing how the device of FIG. 1 may be removed from a postoperative patient without reopening the patient's chest wall.

The risk of atrial fibrillation in postoperative patients is substantially eliminated after 10 to 15 days after surgery. Accordingly, after the risk of atrial fibrillation has been alleviated, the one or more devices 10, 100 will need to be removed from the patient. To prevent further discomfort to the patient, the devices 10, 100 are removable without reopening the patient's chest wall 40. FIG. 6 is a side-by-side flow diagram showing how the devices 10, 100 may be removed from a postoperative patient without reopening the patient's chest wall 40. In the description of the removal method embodiments hereafter described in detail, the alternate embodiment device 100 is included, in each instance, in parentheses as it is removable in a manner similar to that by which the other embodiment device 10 may be removed.

In a first embodiment of the removable method, the pad 12 (spiral shaped pad 82) is pulled along with the electrode portions 22 (wire 84) into the lumen 18 housing the electrode 20 (electrode 80). It should be noted that if the lumens 16, 18 merge at the distal end 15 of the catheter 14 (as shown in FIGS. 1 and 5), this will aid the physician in pulling the pad 12 (spiral shaped pad 82) and electrode portions 22 (wire 84) into the catheter 14. After the pad 12 (pad 82) and electrode portions 22 are (wire 84) pulled into the lumen 18, the device 10 (device 100) can be removed from the patient by pulling the catheter 14 through the chest wall 40. If more than one device 10 (device 100) is used in treating the patient, the additional devices 10 (devices 100) may be removed in a similar manner.

In a second embodiment, the pad 12 (pad 82) is bioabsorbable. In this embodiment, the pad 12 (pad 82) is designed to be bioabsorbed over the time during which the device 10 (device 100) is implanted, i.e., within 30 to 40 days. After the pad 12 (pad 82) has been bioabsorbed, the electrode portions 22 are (wire 84 is) readily pulled into the lumen 18 in the catheter 14 housing the bundled electrode 20 (electrode 80). It should be noted that if the lumens 16, 18 merge at the distal end 15 of the catheter 14 (as shown in FIGS. 1 and 5), this will aid the physician in pulling the electrode portions 22 (wire 84) into the catheter 14. At this time, and similar to the previously described embodiment, the catheter 14 may be pulled through the patient's chest wall 40. Again, if more than one device 10 (device 100) is used in treating the patient, the additional devices 10 (devices 100) may be removed in a similar manner.

In addition to the aforementioned modifications, the invention is not limited to atrial fibrillation. Rather, the device may be used to monitor and control ventricular fibrillation. Further, the device may be used to provide controlled drug delivery to another organ such delivering cancer medication to the pancreas or liver. Accordingly, it should be understood that the apparatus and method described herein are illustrative only and are not limiting upon the scope of the invention, which is indicated by the following claims.

What is claimed is:

1. A device for treating atrial fibrillation in a postoperative cardiac patient, the device comprising:
   a bioabsorbable pad adapted to be placed on an atrial surface of the patient;
   an electrode a distal end of which is provided in the pad, wherein the distal end of the electrode is adapted to deliver a substantially uniform electrical shock to the atrial surface, and wherein a proximal end of the electrode is adapted to be connected to an energy source; and
   a catheter adapted to deliver at least one drug to the pad.

2. The device according to claim 1, wherein the distal end of electrode comprises a plurality of electrode portions.

3. The device according to claim 2, wherein the plurality of electrode portions comprises between 4 and 8 electrode portions arranged in a petal-like arrangement fanning out from a central hub.

4. The device according to claim 3, wherein each of the petal-like electrodes is exposed on one side thereof, wherein an opposite side of the petal-like electrodes is in contact with an underside the pad.

5. The device according to claim 4, wherein an insulating material is provided on a topside of the pad, and wherein an adhesive material is provided on the underside of the pad.

6. The device according to claim 5, wherein the adhesive material is selected from the group consisting of gelatin, silicon, protein polymers, collagen pellets, and thrombin.

7. The device according to claim 4, wherein the pad comprises a plurality of petal-like portions each of which is associated with one of said petal-like electrodes.

8. The device according to claim 7, wherein the pad is formed of a polymeric material.

9. The device according to claim 1, wherein the distal and proximal ends of the electrode are electrically connected by a central wire, and wherein the wire is provided in a lumen in the catheter.

10. The device according to claim 1, wherein the at least one drug comprises at least one anti-arrhythmic drug.

11. The device according to claim 10, wherein the at least one anti-arrhythmic drug is selected from the group consisting of procainamide, amiodarone, a combination of procainamide and at least one other anti-arrhythmic drug, a combination of amiodarone and at least one other anti-arrhythmic drug, and a combination of procainamide, amiodarone and at least one other anti-arrhythmic drug.

12. The device according to claim 10, wherein the at least one drug further comprises at least one anesthetic drug.

13. The device according to claim 10, wherein the anesthetic drug is selected from the group consisting of procaine, lidocaine, a combination of procaine and at least one other anesthetic drug, a combination of lidocaine and at least one other anesthetic drug, and a combination of procaine, lidocaine, and at least one other anesthetic drug.

14. The device according to claim 1, wherein the substantially uniform electrical shock delivered to the atrial surface comprises a predetermined amount of energy of about 1.0 joules and about 3.0 joules.

15. The device according to claim 1, wherein the pad is formed of a polymeric material.

16. The device according to claim 15, wherein the polymeric material is sponge.

17. The device according to claim 15, wherein the polymeric material is knitted or woven.

18. The device according to claim 1, wherein the distal end of electrode and the pad are spiral shaped.

19. The device according to claim 1, further comprising:
   a pacing wire adapted to provide pacing energy to the atrial surface of the patient.

20. A device for treating atrial fibrillation in a postoperative cardiac patient, the device comprising:
   a first bioabsorbable pad adapted to be placed on an atrial surface of a right atrium of the patient;
   a first electrode a distal end of which is provided in the first pad, wherein the distal end of the first electrode is adapted to deliver a substantially uniform electrical shock to the atrial surface of the right atrium, and wherein a proximal end of the first electrode is adapted to be electrically connected to an energy source;
   a second bioabsorbable pad adapted to be placed on an atrial surface of a left atrium of the patient;
   a second electrode a distal end of which is provided in the second pad, wherein the distal end of the second electrode is adapted to deliver a substantially uniform electrical shock to the atrial surface of the left atrium, and wherein a proximal end of the second electrode is adapted to be connected electrically to the energy source; and
   at least one catheter adapted to deliver at least one drug to at least one of said right and left atrial surfaces.

21. The device according to claim 20, wherein each of the distal ends of the first and second electrodes comprises a plurality of electrode portions provided in a fan-like arrangement.

22. The device according to claim 20, wherein each of the electrodes has a central portion between the distal and proximal ends thereof, and wherein the central portion of at least one of said electrodes is provided in a lumen in the catheter.

23. The device according to claim 20, wherein the at least one drug comprises an anti-arrhythmic drug.

24. The device according to claim 23, wherein the at least one drug further comprises an anesthetic drug.

25. The device according to claim 20, wherein the substantially uniform electrical shocks delivered to the atrial surfaces of the right atrium and the left atrium comprise predetermined amounts of energy, and wherein each of the predetermined amounts of energy is between about 1.0 joules and about 3.0 joules.

26. The device according to claim 20, wherein the at least one catheter comprises two catheters, wherein a first of said catheters is adapted to deliver the at least one drug to the right atrial surface, and wherein a second of said catheters is adapted to deliver the at least one drug to the left atrial surface.

27. The device according to claim 26, wherein each of the electrodes has a central portion between the distal and proximal ends thereof, wherein the central portion of the first electrode is provided in a lumen in the first catheter, and wherein the central portion of the second electrode is provided in a lumen in the second catheter.

28. The device according to claim 20, further comprising:
    at least one pacing wire adapted to provide pacing energy to at least one of the right and left atrial surfaces of the patient.

29. A method of treating atrial fibrillation in a postoperative cardiac patient, the method comprising the steps of:
    (a) placing a bioabsorbable pad on an atrial surface of the patient, wherein the pad contains a distal end of an electrode which is adapted to deliver a substantially uniform electrical shock to the atrial surface;
    (b) passing a proximal end of the electrode through a chest wall of the patient;
    (c) connecting the proximal end of the electrode to an energy source;
    (d) monitoring the atrial surface for atrial fibrillation;
    if atrial fibrillation is detected, (e) shocking the atrial surface with a predetermined amount of energy to defibrillate the heart; and
    (f) delivering at least one drug to the pad in contact with the atrial surface via a catheter passing through the chest wall,
    wherein the energy is delivered from the energy source to the atrial surface via the electrode.

30. The method according to claim 29, wherein the predetermined amount of energy is between about 1.0 joules and about 3.0 joules.

31. The method according to claim 29, wherein the distal end of electrode comprises a plurality of electrode portions provided in a fan-like arrangement.

32. The method according to claim 31, wherein the proximal ends of the electrode portions are electrically provided in a bundle in a lumen in the catheter.

33. The method according to claim 32, wherein the method further comprises the step of:
    (h) removing the electrode and the pad from the atrial surface by pulling the electrode and the pad through the catheter.

34. The method according to claim 29, wherein the distal and proximal ends of the electrode are electrically connected by a central wire, and wherein the wire is provided in a lumen in the catheter.

35. The method according to claim 29, wherein the at least one drug comprises an anti-arrhythmic drug.

36. The method according to claim 35, wherein the at least one drug further comprises an anesthetic drug.

37. The method according to claim 29, wherein the at least one drug comprises an anesthetic drug.

38. The method according to claim 37, further comprising the step of:
    (d)(1) anesthetizing locally tissue surrounding the heart with the anesthetic drug before the step of (e) shocking the atrial surface with a predetermined amount of energy to defibrillate the heart.

39. The method according to claim 38, wherein the step of (f) delivering at least one drug to the pad in contact with the atrial surface via a catheter passing through the chest wall comprises:
    (f)(1) medicating the atrial surface with an anti-arrhythmic drug either during or after the step of (e) shocking the atrial surface with a predetermined amount of energy to defibrillate the heart.

40. The method according to claim 29, further comprising the steps of:
    (g) bioabsorbing the pad over a treatment duration; and
    (h) removing the electrode from the atrial surface.

41. The method according to claim 40, wherein the distal and proximal ends of the electrode are electrically connected by a central wire, wherein the wire is provide in a lumen in the catheter, and wherein the step of (h) removing the electrode from the atrial surface comprises:
    (h)(1) pulling the electrode through the catheter.

42. The method according to claim 29, wherein the distal and proximal ends of the electrode are electrically connected by a central wire, and wherein the wire is provide in a lumen in the catheter, and wherein the method further comprises the step of:
    (h) removing the electrode and the pad from the atrial surface by pulling the electrode and the pad through the catheter.

43. The method according to claim 29, wherein the step of (a) placing a bioabsorbable pad on an atrial surface of the patient, comprises the step of:
    (a)(1) adjusting the size of the electrode provided in the pad to correspond to the size of the atrial surface to which the pad is subsequently placed.

44. The method according to claim 29, wherein the step of (f) delivering at least one drug to the pad in contact with the atrial surface via a catheter passing through the chest wall comprises:
    (f)(1) delivering a bolus of the drug to the atrial surface.

45. The method according to claim 29, wherein the step of (f) delivering at least one drug to the pad in contact with the atrial surface via a catheter passing through the chest wall comprises:
    (f)(1) delivering the drug continuously to the atrial surface by means of a pump.

46. The method according to claim 29, further comprising the step of:
    (g) providing pacing energy to the atrial surface of the patient by means of a wire.

47. The method according to claim 46, wherein the wire and the electrode are provided in a catheter extending from the atrial surface of the patient to a location external of the patient's chest wall.

* * * * *